(12) United States Patent
Francke et al.

(10) Patent No.: US 7,020,237 B2
(45) Date of Patent: Mar. 28, 2006

(54) SCANNING-BASED DETECTION OF IONIZING RADIATION FOR TOMOSYNTHESIS

(75) Inventors: Tom Francke, Sollentuna (SE); Skiff Sokolov, Lidingö (SE)

(73) Assignee: Xcounter AB, Danderyd (SE)

( * ) Notice: Subject to any disclaimer, the term of this patent is extended or adjusted under 35 U.S.C. 154(b) by 0 days.

(21) Appl. No.: 10/791,535

(22) Filed: Mar. 3, 2004

(65) Prior Publication Data

US 2005/0152491 A1    Jul. 14, 2005

(30) Foreign Application Priority Data

Jan. 8, 2004 (SE) .................................. 0400010

(51) Int. Cl.
*G01N 23/083* (2006.01)
*G01N 23/00* (2006.01)

(52) U.S. Cl. .............................. 378/23; 378/2
(58) Field of Classification Search .................. 378/4, 378/7, 11, 19, 37, 21–23, 25, 26, 2
See application file for complete search history.

(56) References Cited

U.S. PATENT DOCUMENTS

| | | | | |
|---|---|---|---|---|
| 4,075,492 A | * | 2/1978 | Boyd et al. ...................... | 378/7 |
| 4,315,157 A | * | 2/1982 | Barnes ........................... | 378/10 |
| 4,466,113 A | | 8/1984 | Strecker | |
| 4,969,165 A | * | 11/1990 | Bernardi et al. ............... | 378/13 |
| 5,022,060 A | | 6/1991 | Trotel | |
| 5,126,938 A | | 6/1992 | Oda | |
| 6,118,125 A | | 9/2000 | Carlson et al. | |
| 6,118,841 A | | 9/2000 | Lai | |
| 6,196,715 B1 | * | 3/2001 | Nambu et al. ................. | 378/197 |
| 6,243,438 B1 | | 6/2001 | Nahaliel et al. | |
| 6,335,957 B1 | * | 1/2002 | DiBianca ...................... | 378/19 |
| 6,337,482 B1 | | 1/2002 | Francke et al. | |
| 6,358,282 B1 | | 3/2002 | Wymann | |
| 6,373,065 B1 | | 4/2002 | Francke et al. | |
| 6,414,317 B1 | | 7/2002 | Francke et al. | |
| 6,476,397 B1 | | 11/2002 | Francke | |
| 6,477,223 B1 | | 11/2002 | Francke | |
| 6,518,578 B1 | | 2/2003 | Francke et al. | |
| 6,522,722 B1 | | 2/2003 | Francke | |
| 6,546,070 B1 | | 4/2003 | Francke | |
| 6,628,745 B1 | | 9/2003 | Annis et al. | |

(Continued)

FOREIGN PATENT DOCUMENTS

GB        2070883        2/1981

(Continued)

*Primary Examiner*—Craig E. Church
*Assistant Examiner*—Krystyna Suchecki
(74) *Attorney, Agent, or Firm*—Harness, Dickey & Pierce, P.L.C.

(57) ABSTRACT

An apparatus for obtaining tomosynthesis data of an object comprises a source emitting radiation centered around an axis of symmetry; a radiation detector comprising a stack of line detectors, each being directed towards the source at a respective angle; and a device for moving the source and the radiation detector relative the object linearly in a direction orthogonal to the symmetry axis, while each of the line detectors is adapted to record line images of radiation as transmitted through the object in the respective angle. A device is provided for rotating the radiation detector around a rotation axis orthogonal to the symmetry axis, and the device for moving is further arranged to repeat the essential linear movement of the source and the radiation detector relative the object, while each of the line detectors is adapted to record a further plurality of line images of radiation as transmitted through the object.

24 Claims, 4 Drawing Sheets

U.S. PATENT DOCUMENTS 6,643,352 B1 * 11/2003 Oikawa .................. 378/21
2004/0013225 A1 * 1/2004 Gregerson et al. ........... 378/19
2005/0117707 A1 * 6/2005 Baier et al. ................ 378/156

FOREIGN PATENT DOCUMENTS

WO    WO 01/59480    8/2001

* cited by examiner

SCANNING-BASED DETECTION OF IONIZING RADIATION FOR TOMOSYNTHESIS

FIELD OF THE INVENTION

The invention relates generally to scanning-based apparatuses and methods for obtaining tomosynthesis data for examination of an object.

BACKGROUND OF THE INVENTION AND RELATED ART

An X-ray medical diagnostic method such as mammography is a low-dose procedure that creates one or more images of a part of a patient such as a breast thereof, which is to be examined, e.g. for detection of early stages of cancer.

The mammography diagnostic procedure generally includes obtaining two images of each of the patient's breasts, one from above and one from the side. A physician or radiologist then reviews the images of the breast, i.e., mammograms, to identify any breast cancer.

While this procedure is one of the best methods of detecting early forms of breast cancer, it is still possible for the detection of breast cancer to be missed by a physician or radiologist reviewing the mammograms. For example, breast cancer may be missed by being obscured by radiographically dense, fibroglandular breast tissue.

Tomosynthesis imaging, in which a plurality of images is acquired at different angles, has been studied in an effort to detect early forms of breast cancer. By combining the plurality of images, it is possible to reconstruct any plane in the breast being imaged that is parallel to the detector. The higher number of images is utilized, the better image quality in the reconstructed tomosynthesis images is obtained.

Further, various line detectors for detecting ionizing radiation are known in the art. While such detectors provide for instantaneous one-dimensional imaging, two-dimensional imaging can only be performed by means of scanning the line detector, and optionally the radiation source, in a direction traverse to the one-dimensional detector array. To use such a detector in tomosynthesis, wherein a plurality of images has to be acquired at different angles would be very time consuming.

SUMMARY OF THE INVENTION

A main object of the invention is therefore to provide a scanning-based apparatus and a method, respectively, for obtaining tomosynthesis data of an object at a higher speed than what is obtainable by using scanning-based apparatuses and methods of the prior art.

In this respect there is a particular object to provide such an apparatus and such a method, which are capable of instantaneously recording, by means multiple one-dimensional detectors, multiple one-dimensional images of the object, and, by means of scanning, multiple two-dimensional images of the object, where each of the one-dimensional images of the object is recorded at a different angle.

A further object of the invention is to provide such an apparatus and such a method, which are capable of recording, by means of scanning a number of one-dimensional detectors over the object, a number of two-dimensional images of the object, where each of the two-dimensional images of the object is recorded at a different angle, and where the number of the two-dimensional images is higher than the number of one-dimensional detectors.

A still further object of the invention is to provide such an apparatus and such a method, which are uncomplicated and can produce high-quality two-dimensional tomosynthesis images with high spatial resolution, high signal-to-noise ratio, high dynamic range, high image contrast, and low noise from overlaying tissue.

A yet further object of the invention is to provide such an apparatus and such a method, which are reliable, accurate, and inexpensive.

These objects, among others, are attained by apparatuses and methods as claimed in the appended claims.

The inventors have found that by providing a divergent radiation source emitting radiation centered around an axis of symmetry, and a radiation detector comprising a stack of line detectors, each being directed towards the divergent radiation source to allow a ray bundle of the radiation that propagates in a respective one of a plurality of different angles to enter the line detector after having been transmitted through an object to be examined, and moving the radiation source and the radiation detector relative the object linearly in a direction orthogonal to the axis of symmetry, while each of the line detectors records line images of radiation as transmitted through the object in a respective one of the different angles, a plurality of two-dimensional images can be formed, where each two-dimensional image is formed from a plurality of line images as recorded by a single one of the line detectors.

Thus, a plurality of two-dimensional images at different angles are produced in a single scan, which reduces the detection time by a factor corresponding to the number of two-dimensional images produced.

Preferably, a device is provided for rotating the radiation detector around an axis of rotation being orthogonal to the axis of symmetry, wherein the line detectors, after the rotation, are each directed towards the divergent radiation source to allow a ray bundle of the radiation that propagates in a respective one of a further plurality of different angles to enter the line detector, and the device for moving is further arranged to repeat the linear movement of the divergent radiation source and the radiation detector relative the object, while each of the line detectors is adapted to record a further plurality of line images of radiation as transmitted through the object in a respective one of the further plurality of different angles.

The data from the apparatus is excellent to be used in tomosynthesis or laminographic imaging.

The line detectors uses are preferably, but not exclusively, gaseous-based parallel plate detectors. Other line detectors that may be used include, scintillator-based arrays, CCD arrays, TFT- and CMOS-based detectors, liquid detectors, and diode arrays, e.g. PIN-diode arrays with edge-on, near edge-on or perpendicular incidence of X-rays. A collimator structure may be arranged in front of the detectors to partly reject scattered X-rays.

Further characteristics of the invention, and advantages thereof, will be evident from the detailed description of preferred embodiments of the present invention given hereinafter and the accompanying FIGS. 1–4, which are given by way of illustration only, and thus are not limitative of the present invention.

DESCRIPTION OF PREFERRED EMBODIMENTS

Figure 1:
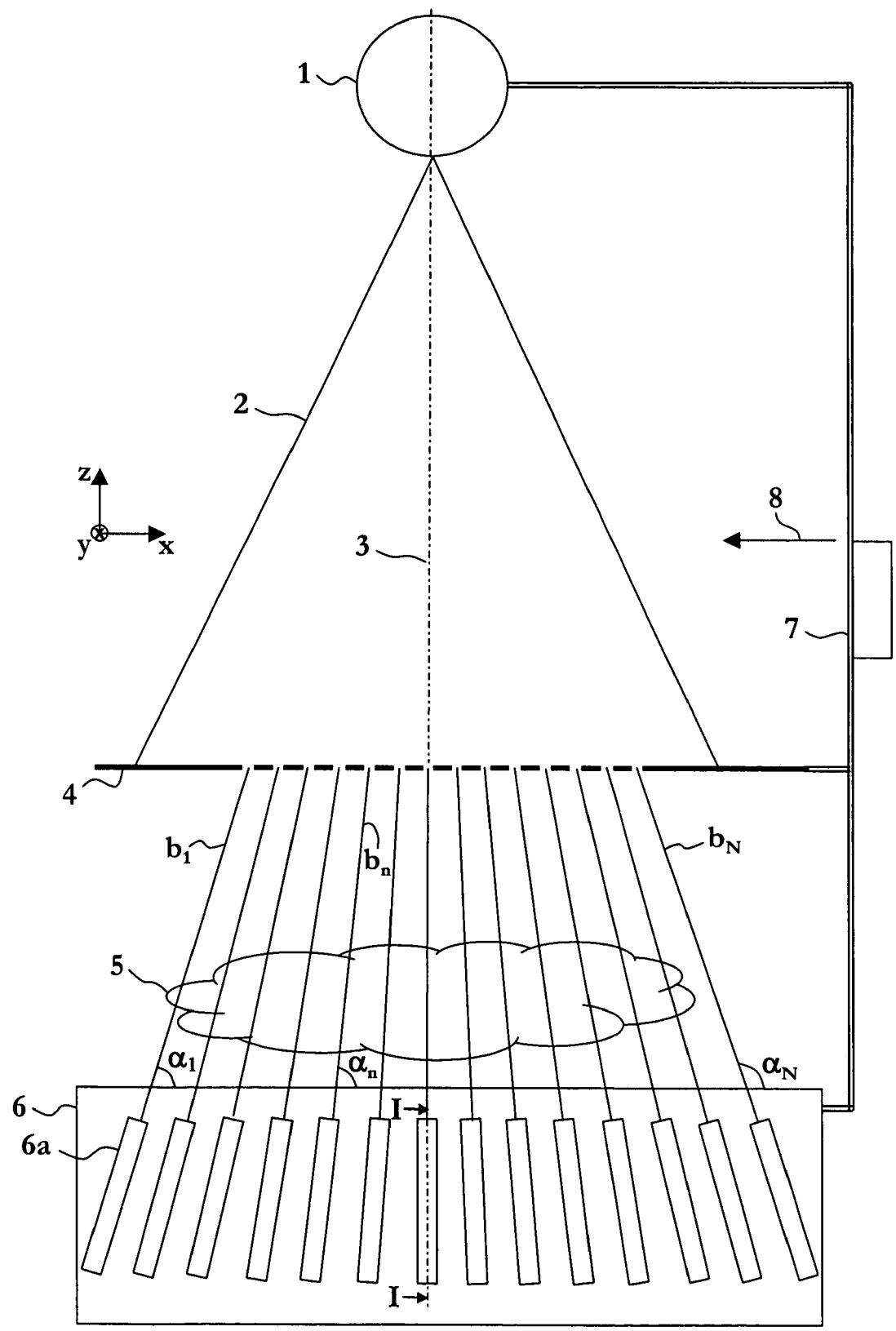
FIG. 1 illustrates schematically, in a top view, an apparatus for obtaining tomosynthesis data for x-ray examination of an object according to a preferred embodiment of the present invention.

The apparatus of FIG. 1 comprises a divergent X-ray source 1, which produces X-rays 2 centered around an axis of symmetry 3 (parallel with the z axis), a collimator 4, a radiation detector 6, and a device 7 for rigidly connecting the X-ray source 1, the collimator 4, and the radiation detector 6 to each other and moving the X-ray source 1, the collimator 4, and the radiation detector 6 essentially linearly in direction 8 (typically parallel with the x axis) essentially orthogonal to the axis of symmetry 3 to scan an object 5, which is to be examined.

The radiation detector 6 comprises a stack of line detectors 6a, each being directed towards the divergent radiation source 1 to allow a respective ray bundle b1, . . . , $b_n$, . . . , $b_N$ of the radiation 2 that propagates in a respective one of a plurality of different angles $\alpha_1$, . . . , $\alpha_n$, . . . , $\alpha_N$ with respect to the front surface of the radiation detector 6 to enter the respective line detector 6a. The line detectors 6a are extending in the y direction to record line images extending in the y direction.

The collimator 4 may be a thin foil of e.g. tungsten with narrow radiation transparent slits etched away, the number of which corresponds to the number of line detectors 6a of the radiation detector 6. The slits are aligned with the line detectors 6a so that X-rays passing through the slits of the collimator 4 will reach the detector units 6a, i.e. as the respective ray bundles $b_1$, . . . , $b_n$, . . . , $b_N$. The collimator 4, which is optional, prevents radiation, which is not directed directly towards the line detectors 6a, from impinging on the object 5, thereby reducing the radiation dose to the object. This is advantageous in all applications where the object is a human or an animal, or parts thereof.

During scanning the device 7 moves the radiation source 1, the collimator 4, and the radiation detector 6 relative the object 5 in a linear manner parallel with the front of the radiation detector as being indicated by arrow 8, while each of the line detectors 6a records a plurality of line images of radiation as transmitted through the object 5 in a respective one of the different angles $\alpha_1$, . . . , $\alpha_n$, . . . , $\alpha_N$.

The scanning of the object 5 is preferably performed a length, which is sufficiently large so that each one of the line detectors 6a can be scanned across the entire object of interest to obtain, for each of the line detectors 6a, a two-dimensional image of radiation as transmitted through the object 5 in a respective one of the different angles $\alpha_1$, . . . , $\alpha_n$, . . . , $\alpha_N$.

Figure 2A:
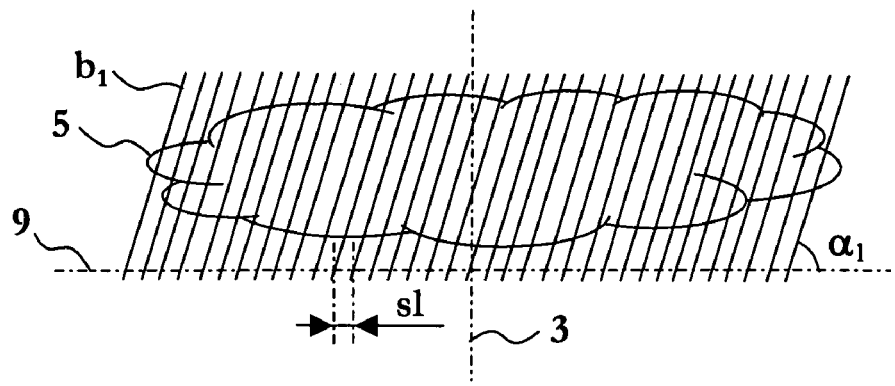
FIGS. 2a–c illustrate each schematically, in a top view, a particular X-ray bundle as it traverses the examination object during a first scanning movement by the apparatus of FIG. 1.
Figure 2B:
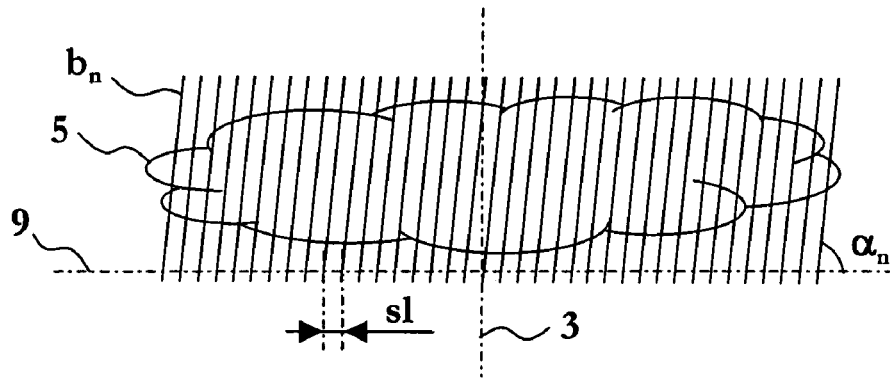
Figure 2C:
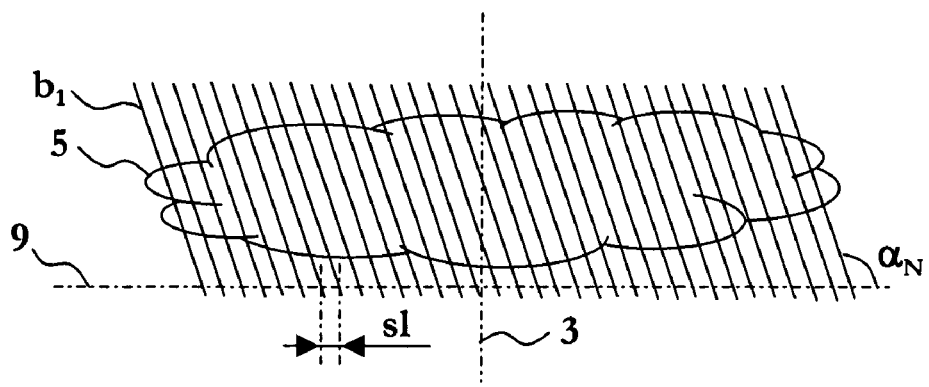

In FIGS. 2a–c three different X-ray bundles $b_1$, $b_n$, and $b_N$ are schematically illustrated as they traverse the examination object 5 during scanning by the apparatus of FIG. 1. Reference numeral 9 indicates a plane parallel with the x axis, which coincides with the scanning direction 8 and with the front of the radiation detector 2.

As can be seen in FIGS. 2a–c each line detector/X-ray bundle pair produces a complete two-dimensional image at a distinct one of the different angles. FIG. 2a illustrates the formation of a two-dimensional image of radiation transmitted through the object at an angle $\alpha_1$, FIG. 2b illustrates the formation of a two-dimensional image of radiation transmitted through the same object, but at an angle $\alpha_n$, and FIG. 2c illustrates the formation of a similar two-dimensional image, but at an angle $\alpha_N$.

Preferably, the different angles are distributed over an angular range $\alpha_N$–$\alpha_1$ of at least 5°, preferably at least 10°, and most preferably at least 15° depending on the application or kind of examination in order to obtain high-quality tomosynthesis data for examination of the object. The number of line detectors 6a in the stack of line detectors is at least 3, preferably at least 10, and most preferably at least 25 depending on the number of images recorded at different angles, which is required during the examination.

The scanning step, in FIGS. 2a–c denoted by sl, depends on the spatial resolution of the two-dimensional images formed from the one-dimensional recordings. Typically, the scanning step sl can be about 10–500 microns, and the individual detecting elements of each of the line detectors can be of similar size.

Advantageously, the device 7 for performing the scanning movement, or other device (not illustrated), is capable of rotating the radiation source 1, the collimator 4, and the radiation detector 6 an angle $\Delta$ around an axis of rotation passing e.g. through the radiation source 1 or other point, and being orthogonal to the axis of symmetry 3, and preferably parallel with the y axis. The angle $\Delta$ is preferably smaller than the difference between two one adjacent ones of the different angles $\alpha_1$, . . . , $\alpha_n$, . . . , $\alpha_N$.

The radiation source 1 may, however, be kept still during the rotation if the line detectors 6a, after the rotation, are still within the solid angle of radiation as emitted by the radiation source 1.

The device 7 for moving then repeats the linear movement of the radiation source 1, the collimator 4, and the radiation detector 6 relative the object 5 in a second scan, while each of the line detectors records further multiple line images of radiation as transmitted through the object 5 in a respective one of the further different angles $\alpha_1+\Delta$, . . . , $\alpha_n+\Delta$, . . . , $\alpha_N+\Delta$.

Figure 3A:
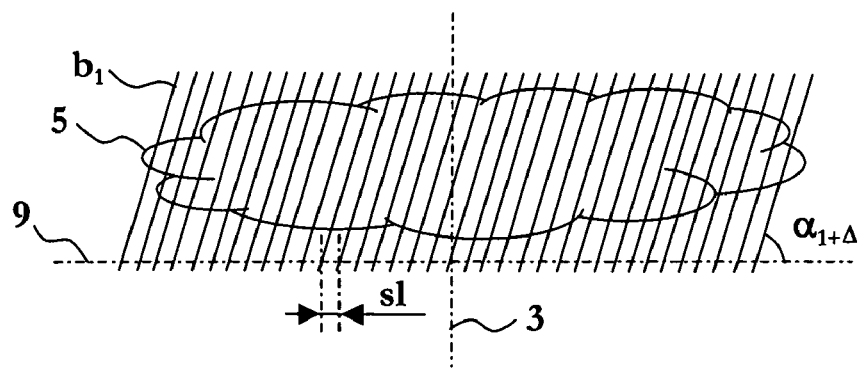
FIGS. 3a–c illustrate each schematically, in a top view, a particular X-ray bundle as it traverses the examination object during a second scanning movement by the apparatus of FIG. 1.
Figure 3B:
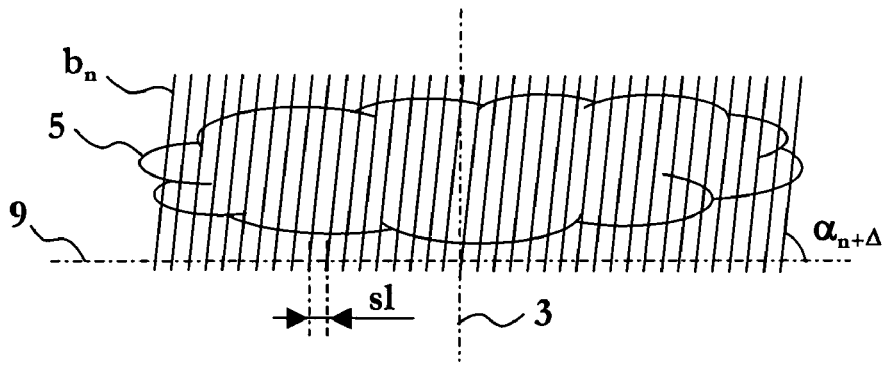
Figure 3C:
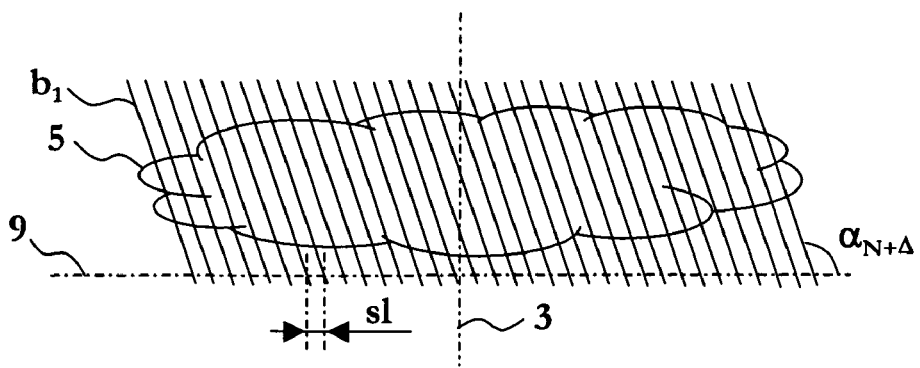

In FIGS. 3a–c three different X-ray bundles $b_1$, $b_n$, and $b_N$ are schematically illustrated as they traverse the examination object 5 during the second scanning by the apparatus of FIG. 1. Reference numeral 9 indicates as in FIG. 2 a plane parallel with the x axis, which here slightly deviates from the scanning direction 8 and from the front of the radiation detector 2 due to the rotation.

As can be seen in FIGS. 3a–c each line detector/X-ray bundle pair produces a complete two-dimensional image at a distinct one of the different angles. FIG. 3a illustrates the formation of a two-dimensional image of radiation transmitted through the object at an angle $\alpha_1+\Delta$, FIG. 3b illustrates the formation of a two-dimensional image of radiation transmitted through the same object, but at an angle $\alpha_n+\Delta$, and FIG. 3c illustrates the formation of a similar two-dimensional image, but at an angle $\alpha_N+\Delta$.

Thus, two linear scans with a slight rotation therein between provide for the formation of 2N two-dimensional images at the different angles $\alpha_1$, $\alpha_1+\Delta$, . . . , $\alpha_n$, $\alpha_n+\Delta$, . . . , $\alpha_N$, $\alpha_N+\Delta$. Similarly, the rotation and linear scanning may be repeated P times to obtain P×N two-dimensional images. In such a manner a large number of images at different angles may be obtained by using a limited number of line detectors. Hereby, a low cost radiation detector can be provided to the cost of a prolonged scanning and examination time. The total radiation dose to the object 5 during the examination has, however, not necessarily to be increased.

Alternatively, or additionally, the rotation may be performed around an axis of rotation, which is parallel with the x axis, between linear scans of the above-described kind.

The more images at different angles are provided, the smaller is the noise from overlaying objects in the reconstructed tomosynthesis image.

In another embodiment of the invention two or more linear scans as disclosed above are performed, and between each of the linear scans a rotation of the above-kind is performed, but where the rotation is larger than the angle range $\alpha_N - \alpha_1$ of the different angles $\alpha_1, \ldots, \alpha_n, \ldots, \alpha_N$.

In such a manner the obtained effective opening angle of the radiation detector 6 is made larger (two times for two linear scans) without that the radiation detector 6 has to be made larger, or include more line detectors 6a. If two linear scans are performed with a rotation of the radiation source 1, the collimator 4, and the radiation detector 6 an angle $\alpha_N - \alpha_1 + \gamma$ therein between, 2N two-dimensional images can be recorded at the different angles $\alpha_1, \ldots, \alpha_n, \ldots, \alpha_N$, $\alpha_1 + \alpha_N - \alpha_1 + \gamma, \ldots, \alpha_n + \alpha_N - \alpha_1 + \gamma, \ldots, \alpha_N + \alpha_N - \alpha_1 + \gamma$ or angles $\alpha_1, \ldots, \alpha_n, \ldots, \alpha_N, \alpha_N + \gamma, \ldots, \alpha_n + \alpha_N - \alpha_1 + \gamma, \ldots, 2\alpha_N - \alpha_1 + \gamma$.

It shall be noted that the present invention is applicable to any kind of examination employing tomosynthesis or laminographic imaging, including e.g. mammography examination and other soft tissue examinations.

A preferred line detector for use in the present invention is a gaseous-based parallel plate detector, preferably provided with an electron avalanche amplifier. Such a gaseous-based parallel plate detector is an ionization detector, wherein electrons freed as a result of ionization by ionizing radiation are accelerated in a direction essentially perpendicular to the direction of the radiation.

Figure 4:
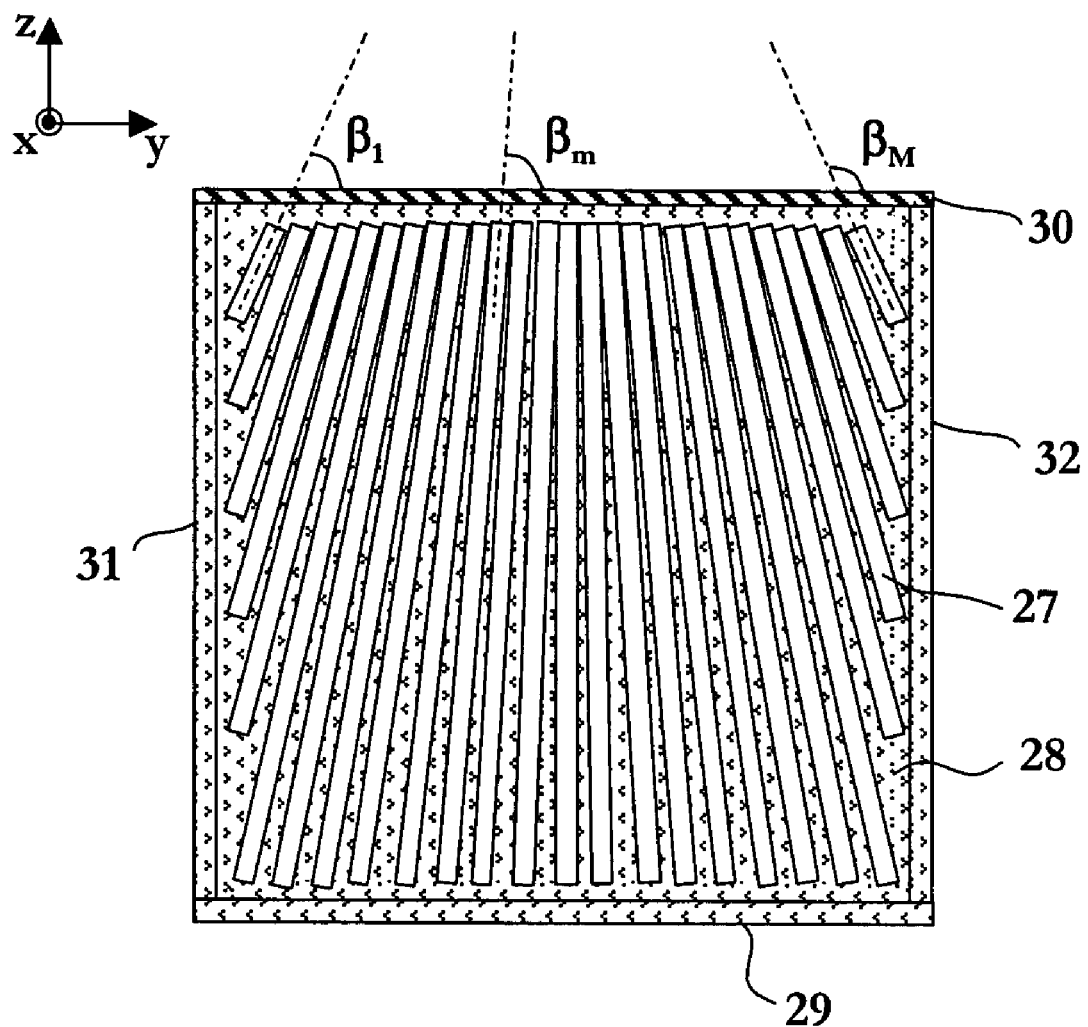
FIG. 4 illustrates schematically a cross-sectional view of a line detector of FIG. 1 as taken along the line I—I.

A cross-sectional view of a line detector of FIG. 1 as taken along the line I—I is schematically illustrated in FIG. 4.

The line detector comprises a window 30 for entry of a ray bundle, and a row of elongated individual conductive detector elements or strips 27 arranged on a dielectric substrate 28. Preferably, the elements or strips 27, which each is capable of separately detecting incident radiation photons, also constitute an anode of the line detector to attract the electrons released during ionization of the ionizable gas in the line detector. Preferably, the dielectric substrate 28 and the window 30 define, together with sidewalls 29, 31, 32 and a non-illustrated dielectric cathode substrate, a gas-tight confinement capable of being filled with the ionizable gas. Alternatively, the line detector is arranged within an external gas-tight casing (not illustrated).

Note that the individual conductive detector/anode elements 27 are arranged side by side in a row parallel with the y direction, and define a respective angle $\beta_1, \ldots, \beta_m, \ldots, \beta_M$ with respect to the xz plane so that all the detector/anode elements 27 point towards the X-ray source 1 to avoid any parallax errors caused by the divergent radiation. As a result different detector/anode elements 27 detect different angular portions $\beta_1, \ldots, \beta_m, \ldots, \beta_M$ of the ray bundle entered into the line detector.

For further details regarding such kind of gaseous-based line detectors for use in the present invention, reference is made to the following U.S. Patents by Tom Francke et al. and assigned to XCounter AB of Sweden, which patents are hereby incorporated by reference: U.S. Pat. Nos. 6,546,070; 6,522,722; 6,518,578; 6,118,125; 6,373,065; 6,337,482; 6,385,282; 6,414,317; 6,476,397; and 6,477,223.

It shall particularly be pointed out that such kind of detector is very efficient in preventing Compton scattered radiation from being detected. This property is of outermost importance to obtain high-quality tomosynthesis data.

The distance between the parallel plates, i.e. electrodes, of the line detector may be below about 2 mm, preferably below about 1 mm, more preferably below about 0.5 mm, and most preferably between about 0.1 mm and 0.5 mm. XCounter AB has recently begun to verify the Compton scattering rejection characteristics of the line detector experimentally and good contrast has been observed using a wide X-ray spectrum of high energy X-rays, at which conditions a conventional detector system would not be capable to see any structure at all. It is believed that the above-depicted gaseous-based line detector discriminates more than 99% of the scattered photons; and by proper design it is assumed that about 99.9% or more of the scattered photons can be prevented from being detected.

It shall, nevertheless, be realized that any other type of detector may be used in the present invention. Such line detectors include scintillator-based arrays, CCD arrays, TFT- and CMOS-based detectors, liquid detectors, and solid-state detectors such as one-dimensional PIN-diode arrays with edge-on, near edge-on or perpendicular incidence of X-rays, possibly with a collimator structure in front to partly reject scattered X-rays.

It shall further be noted that that the device 7 for rigidly connecting the X-ray source 1, the collimator 4, and the radiation detector 6 may be exchanged for separate devices (not illustrated) for the X-ray source 1, the collimator 4, and the radiation detector 6, which may be controlled electronically to obtain synchronous movements of the separate devices to obtain similar scanning movement. Yet alternatively, the apparatus of FIG. 1 can be modified so the object 5 is moved during scanning, while the radiation source 1, the collimator 4, and the radiation detector 6 are kept at rest.

It shall still further be noted that instead of performing linear scans for each rotation, the linear scanning may be performed stepwise, and at each such linear scanning step measurements are made for different rotations. The result is identical, but the measurements are performed in different order. It shall be noted that the present patent document covers both these measurements.

It shall yet further be noted that in an alternative embodiment of the present invention the linear scanning is performed in the y direction and the rotation between the linear scannings is performed around an axis parallel with the x axis. This calls for a very short distance between the line detectors in the stack since one detector strip from each line detector provides the instantaneous one-dimensional image. One complete scan in the y direction involves that each of the detector strips of each of the line detectors is moved across the complete object. The strips of the plurality of line detectors, which are inclined to the xz plane with the angle $\beta_1$, record, during the scan, one two-dimensional image, the adjacent strips record another two-dimensional image at a different angle, etc. After the first scan the detector is rotated an angle $+\Delta$ around an axis parallel with the x axis. During the second scan, the strips of the plurality of line detectors are inclined to the xz plane with $\beta_1 + \Delta, \ldots, \beta_m + \Delta, \ldots, \beta_M + \Delta$. Thus, two linear scans with a slight rotation therein between provide for the formation of 2M two-dimensional images at the different angles $\beta_1, \beta_1 + \Delta, \ldots, \beta_m, \beta_m + \Delta, \ldots, \beta_M, \beta_M + \Delta$. Similarly, the rotation and linear scanning may be repeated P times to obtain P×M two-dimensional images.

What is claimed is:

1. A scanning-based apparatus for obtaining tomosynthesis data of an object comprising:
   a divergent radiation source emitting X-ray radiation centered around an axis of symmetry;
   a radiation detector comprising a stack of line detectors, each being directed towards the divergent radiation source to allow a ray bundle of said X-ray radiation that propagates in a respective one of a plurality of different angles to enter the line detector;
   an object area arranged in the radiation path between said divergent radiation source and said radiation detector for housing said object; and
   a first movement device that moves said divergent radiation source and said radiation detector relative to said object essentially linearly in a direction essentially orthogonal to said axis of symmetry, while each of said line detectors records a plurality of line images of X-ray radiation as transmitted through said object in a respective one of said plurality of different angles, wherein
   said divergent radiation source and said radiation detector are moved relative to said object a length which is sufficient for scanning each of said line detectors across the entire object to obtain, for each of said line detectors, a two-dimensional image of X-ray radiation as transmitted through said object in a respective one of said plurality of different angles, wherein
   said scanning-based apparatus further comprises a second movement device that rotates said divergent radiation source and said radiation detector relative to said object an angle around an axis of rotation orthogonal to said axis of symmetry, the line detectors being, after said rotation, each directed towards the divergent radiation source to allow a ray bundle of said X-ray radiation that propagates through said object in a respective one of a further plurality of different angles to enter the line detector, and
   said first movement device moves once more said divergent radiation source and said radiation detector relative to said object essentially linearly in a direction essentially orthogonal to said axis of symmetry, while each of said line detectors records a plurality of line images of X-ray radiation as transmitted through said object in a respective one of said further plurality of different angles, wherein said divergent radiation source and said radiation detector are moved relative to said object a length which is sufficient for scanning each of said line detectors across the entire object to obtain, for each of said line detectors, a two-dimensional image of X-ray radiation as transmitted through said object in a respective one of said further plurality of different angles to thereby obtain said tomosynthesis data.

2. The apparatus of claim 1 wherein said axis of rotation is passing through said divergent radiation source.

3. The apparatus of claim 1 wherein
   said second movement device is adapted to repeatedly rotate said radiation detector around said axis of rotation, the line detectors being, after each of said rotations, each directed towards the divergent radiation source to allow a ray bundle of said radiation that propagates in a respective angle to enter the line detector; and
   said first movement device is adapted, after each of said rotations, to repeat the essentially linear movement of said divergent radiation source and said radiation detector relative to said object, while each of said line detectors is adapted to record line images of radiation as transmitted through said object in a respective angle.

4. The apparatus of claim 1 wherein said line detectors are oriented to detect line images extending in a direction essentially orthogonal to said axis of symmetry and essentially orthogonal to the direction, in which said first movement device moves said divergent radiation source and said radiation detector relative to said object.

5. The apparatus of claim 4 wherein said direction, in which said line images extend, is parallel with said axis of rotation.

6. The apparatus of claim 1 wherein
   said line detectors are oriented to detect line images extending in a direction essentially orthogonal to said axis of symmetry and essentially parallel with the direction, in which said first movement device moves said divergent radiation source and said radiation detector relative said object; and
   said direction, in which said line images extend, is essentially orthogonal to said axis of rotation.

7. The apparatus of claim 1 wherein said angle around said axis of rotation is smaller than a difference between two adjacent ones of said plurality of different angles.

8. The apparatus of claim 1 wherein said angle around said axis of rotation is equal to, or larger than, an angular range, over which said plurality of different angles is distributed.

9. The apparatus of claim 1 wherein said plurality of different angles is distributed over an angular range of at least 5°.

10. The apparatus of claim 1 wherein said plurality of different angles is distributed over an angular range of at least 10°.

11. The apparatus of claim 1 wherein said plurality of different angles is distributed over an angular range of at least 15°.

12. The apparatus of claim 1 wherein the number of line detectors in said stack of line detectors is at least 3.

13. The apparatus of claim 1 wherein the number of line detectors in said stack of line detectors is at least 10.

14. The apparatus of claim 1 wherein the number of line detectors in said stack of line detectors is at least 25.

15. The apparatus of claim 1 wherein
   said divergent radiation source is an X-ray source; and
   said line detectors are gaseous-based ionization detectors, wherein electrons freed as a result of ionization by a respective ray bundle are accelerated in a direction essentially perpendicular to the direction of that ray bundle.

16. The apparatus of claim 15 wherein said gaseous-based ionization detectors are electron avalanche detectors.

17. The apparatus of claim 1 wherein said line detectors are each any of a diode array, a scintillator-based array, a CCD array, a TFT- or CMOS-based detector, or a liquid detector.

18. The apparatus of claim 1 comprising a collimator arranged in the radiation path between said radiation source and said object area, said collimator preventing radiation, which is not directed towards said line detectors, from impinging on said object, thereby reducing the radiation dose to said object.

19. A scanning-based method for obtaining tomosynthesis data of an object using a divergent radiation source, which emits X-ray radiation centered around an axis of symmetry; and a radiation detector comprising a stack of line detectors, each being directed towards the divergent radiation source to allow a ray bundle of said X-ray radiation that propagates in a respective one of a plurality of different angles to enter the line detector, said method comprising the steps of:

arranging said object in the radiation path between said divergent radiation source and said radiation detector;

moving said divergent radiation source and said radiation detector relative to said object essentially linearly in a direction essentially orthogonal to said axis of symmetry, while, by each of said line detectors, recording a plurality of line images of radiation as transmitted through said object in a respective one of said plurality of different angles;

wherein said moving includes moving said divergent radiation source and said radiation detector relative to said object a length which is sufficient for scanning each of said line detectors across the entire object to obtain, for each of said line detectors, a two-dimensional image of X-ray radiation as transmitted through said object in a respective one of said plurality of different angles, wherein rotating said radiation detector an angle around an axis of rotation orthogonal to said axis of symmetry, the line detectors being, after said rotation, each directed towards the divergent radiation source to allow a ray bundle of said radiation that propagates in a respective one of a further plurality of different angles to enter the line detector; and repeating the essentially linear movement of said divergent radiation source and said radiation detector relative to said object, moving once more said divergent radiation source and said radiation detector relative to said object essentially linearly in a direction essentially orthogonal to said axis of symmetry, while each of said line detectors records a plurality of line images of X-ray radiation as transmitted through said object in a respective one of said further plurality of different angles, wherein said divergent radiation source and said radiation detector are moved relative said object a length which is sufficient for scanning each of said line detectors across the entire object to obtain, for each of said line detectors, a two-dimensional image of X-ray radiation as transmitted through said object in a respective one of said further plurality of different angles to thereby obtain said tomosynthesis data.

20. The method of claim 19 wherein said axis of rotation is passing through said divergent radiation source.

21. The method of claim 19 wherein said angle around said axis of rotation, which said radiation detector is rotated, is smaller than a difference between two adjacent ones of said plurality of different angles.

22. The method of claim 19 wherein said angle around said axis of rotation, which said radiation detector is rotated, is equal to, or larger than, an angular range, over which said plurality of different angles is distributed.

23. A scanning-based apparatus for obtaining tomosynthesis data of an object comprising:

a divergent radiation source emitting X-ray radiation centered around an axis of symmetry;

a radiation detector comprising a stack of line detectors, each being directed towards the divergent radiation source to allow a ray bundle of said X-ray radiation that propagates in a respective one of a plurality of different angles to enter the line detector;

an object area arranged in the radiation path between said divergent radiation source and said radiation detector for housing said object; and a first movement device that rotates said divergent radiation source and said radiation detector relative said object an angle around an axis of rotation orthogonal to said axis of symmetry to reach a position where a ray bundle of said X-ray radiation that propagates through said object in a respective one of a further plurality of different angles enters the line detector, wherein each of said line detectors records one line image of X-ray radiation as transmitted through said object in a respective one of said plurality of different angles and one line image of X-ray radiation as transmitted through said object in a respective one of said further plurality of different angles and, a second movement device that repeatedly moves said divergent radiation source and said radiation detector relative to said object essentially linearly in a direction essentially orthogonal to said axis of symmetry, wherein subsequent to each of said essentially linear movements, said first movement device rotates said divergent radiation source and said radiation detector relative said object, wherein each of said line detectors records a line image of X-ray radiation as transmitted through said object in a respective one of said plurality of different angles and a line image of X-ray radiation as transmitted through said object in a respective one of said further plurality of different angles, and said second movement device moves said divergent radiation source and said radiation detector relative to said object essentially linearly in a direction essentially orthogonal to said axis of symmetry repeatedly an accumulated length which is sufficient for scanning each of said line detectors across the entire object to obtain, for each of said line detectors, one two-dimensional image of X-ray radiation as transmitted through said object in a respective one of said plurality of different angles and one two-dimensional image of X-ray radiation as transmitted through said object in a respective one of said further plurality of different angles to thereby obtain said tomosynthesis data.

24. A method for obtaining tomosynthesis data of an object comprising the steps of:

emitting X-ray radiation centered around an axis of symmetry by a divergent radiation source;

directing each line detector of a stack of line detectors towards the divergent radiation source to allow a ray bundle of said X-ray radiation that propagates in a respective one of a plurality of different angles to enter the line detector;

arranging an object area in the radiation path between said divergent radiation source and said stack of line detectors for housing said object; and rotating said divergent radiation source and said stack of line detectors relative to said object an angle around an axis of rotation orthogonal to said axis of symmetry to reach a position where a ray bundle of said X-ray radiation that propagates through said object in a respective one of a further plurality of different angles enters the line detector, wherein each of said line detectors records one line image of X-ray radiation as transmitted through said object in a respective one of said plurality of different angles and one line image of X-ray radiation as transmitted through said object in a respective one of said further plurality of different angles; and repeatedly moving said divergent radiation source and said stack of line detectors relative to said object essentially linearly in a direction essentially orthogonal to said axis of symmetry, wherein repeatedly rotating subsequent to each of said essentially linear movements, said divergent radiation source and said stack of line detectors relative to said object, wherein each of said line detectors records a line image of X-ray radiation as transmitted through said object in a respective one of said plurality of different angles and a line image of X-ray radiation as transmitted through said object in a respective one of said further plurality of different angles; and said repeatedly moving includes moving said divergent radiation source and said stack of line detectors relative to said object essentially linearly in a direction essentially orthogonal to said axis of symmetry repeatedly an accumulated length which is sufficient for scanning each of said line detectors across the entire object to obtain, for each of said line detectors, one two-dimensional image of X-ray radiation as transmitted through said object in a respective one of said plurality of different angles and one two-dimensional image of X-ray radiation as transmitted through said object in a respective one of said further plurality of different angles to thereby obtain said tomosynthesis data.

* * * * *